United States Patent [19]

Ohmachi et al.

[11] Patent Number: 5,536,623
[45] Date of Patent: Jul. 16, 1996

[54] METHOD OF PRODUCING HIGHLY WATER-SOLUBLE CYCLODEXTRIN COMPLEX

[75] Inventors: Yoshihiro Ohmachi, Tsukuba; Yoshihiko Tsugawa, Kashiwara; Akihiro Nagai, Toyono-gun, all of Japan

[73] Assignee: Takeda Chemical Industries, Ltd., Osaka, Japan

[21] Appl. No.: 11,457

[22] Filed: Jan. 29, 1993

[30] Foreign Application Priority Data

Jan. 30, 1992 [JP] Japan .................................. 4-015236
Dec. 11, 1992 [JP] Japan .................................. 4-332021

[51] Int. Cl.⁶ ............................ A61K 47/48; C08B 37/16
[52] U.S. Cl. ............................................. 252/315.1
[58] Field of Search ........................................ 252/315.1

[56] References Cited

U.S. PATENT DOCUMENTS 5,196,406   3/1993   Kamei et al. ............................ 514/58

FOREIGN PATENT DOCUMENTS 0335545   10/1989   European Pat. Off. .
0447351    9/1991   European Pat. Off. .
0461427   12/1991   European Pat. Off. .
0519428   12/1992   European Pat. Off. .
63-135402   6/1988   Japan .

OTHER PUBLICATIONS

Y. Mizuno, et al., "Syntheses of Potential Antimetabolites. XVII.", *Chemical and Pharmaceutical Bulletin*, vol. 23, 1975, pp. 1411 to 1430.

*Primary Examiner*—Gary Geist
*Assistant Examiner*—Catherine Kilby Scalzo
*Attorney, Agent, or Firm*—David G. Conlin; Peter F. Corless

[57] ABSTRACT

The present invention provides 1) a method of producing a complex of a fumagillol derivative of the formula:

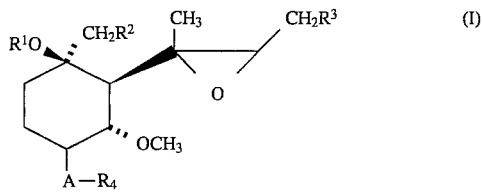

wherein $R^1$ is hydrogen; $R^2$ is halogen, $N(O)mR^5R^6$, $N+R^5R^6R^7 \cdot X^-$ or $S(O)nR^5$, wherein $R^5$, $R^6$ and $R^7$ are independently an optionally substituted hydrocarbon group or an optionally substituted heterocyclic group; $X^-$ is a counter anion; m is 0 or 1; n is an integer of 0 to 2; and $R^5$ and $R^6$ together with the adjacent nitrogen or sulfur atom may form an optionally substituted nitrogen- or sulfur-containing heterocyclic group which may form a condensed ring; or $R^1$ and $R^2$ are combined to represent a chemical bond; $R^3$ is 2-methyl-1-propenyl group or isobutyl group; A is oxygen or $NR^8$, wherein $R^8$ is hydrogen or an optionally substituted lower alkyl or aryl group; and $R^4$ is hydrogen, an optionally substituted hydrocarbon group or an optionally substituted acyl group; or a physiologically acceptable salt thereof, with a highly water-soluble cyclodextrin derivative, which comprises mixing the fumagillol derivative or a physiologically acceptable salt thereof with the highly water-soluble cyclodextrin derivative into an aqueous solution, the concentration of the highly water-soluble cyclodextrin derivative being at about 100 mg/ml or more, and 2) the complex of the fumaggillol derivative (I) or physiologically acceptable salt thereof with the highly water-soluble cyclodextrin derivative obtained by the production method 1).

The complex of the fumagillol derivative (I) or physiologically acceptable salt thereof with the highly water-soluble cyclodextrin derivative is highly soluble in water, highly stable in storage and can be used as a preparation for injection.

5 Claims, No Drawings

METHOD OF PRODUCING HIGHLY WATER-SOLUBLE CYCLODEXTRIN COMPLEX

FIELD OF THE INVENTION

The present invention relates to a method of producing a complex of a fumagillol derivative (or a salt thereof) which inhibits anglogenesis and has therapeutic and prophylactic effects on various inflammatory diseases (e.g., arthrorheumatis), diabetic retinopathy and tumors (e.g., cancer such as mastocarcinoma, hepatoma, large intestinal cancer and kaposi's sarcoma) with a highly water-soluble cyclodextrin wherein the water solubility of said fumagillol derivative is enhanced, in order to promote its absorption and heighten its pharmacological activity.

BACKGROUND OF THE INVENTION

Conventional methods of forming a cyclodextrin complex or inclusion compound of a drug slightly soluble in water include the method in which a saturated aqueous solution of the drug and cyclodextrin is cooled to precipitate the complex, the method in which an aqueous solution of the drug and cyclodextrin is lyophilized [M. Kurozumi et al., Chemical and Pharmaceutical Bulletin, 23, 1421 (1975)], and the mixed milling method [Y. Nakai et al., Chemical and Pharmaceutical Bulletin, 26, 2419 (1978)]. However, the solubility of the complex of a slightly water-soluble drug and cyclodextrin as obtained by these methods is not sufficient to permit its use as an injection. Also, drug stability is lessened in some cases.

Further, Japanese published unexamined patent application No. 63-135402 mentions the pharmaceutical composition which comprises maltosyl-β-cyclodextrin and at least one compound selected from the group consisting of digitonin, nifedipine, flurubiprofen, isosorbide nitrate, phenytoin, progesterone and testosterone. However, the reference is silent about a fumagillol derivative.

There is demand for the development of a complex usable as a preparation for injection and of a method of industrial production thereof by increasing the solubility and stability of the fumagillol derivative, a drug which is only slightly soluble in water.

In view of this situation, the present inventors investigated increasing the water solubility of a fumagillol derivative (or a salt thereof), which is slightly soluble in water, and found that a liquid complex with markedly improved solubility of a fumagillol derivative can be obtained by suspending the fumagillol derivative in an aqueous solution containing highly water-soluble cyclodextrin derivative at about 100 mg/ml or more, stirring the suspension to obtain a solution, and filtering the solution to remove the undissolved fumagillol derivative upon completion of the progress of dissolution, and that a powdered complex with markedly improved water solubility of the fumagillol derivative can be obtained by drying the liquid. The inventors made further investigations based on this finding, and developed the present invention.

SUMMARY OF THE INVENTION

The present invention relates to:

1. A method of producing a complex of a fumagillol derivative of the formula:

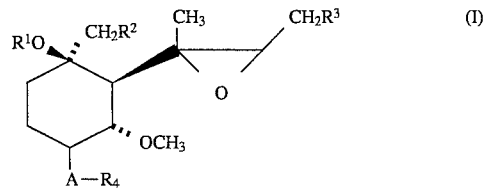

wherein $R^1$ is hydrogen; $R^2$ is halogen, $N(O)mR^5R^6$, $N+R^5R^6R^7 \cdot X-$ or $S(O)nR^5$, wherein $R^5$, $R^6$ and $R^7$ are independently an optionally substituted hydrocarbon group or an optionally substituted heterocyclic group; $X-$ is a counter anion; m is 0 or 1; n is an integer of 0 to 2; and $R^5$ and $R^6$ together with the adjacent nitrogen or sulfur atom may form an optionally substituted nitrogen- or sulfur-containing heterocyclic group which may form a condensed ring; or $R^1$ and $R^2$ are combined to represent a chemical bond; $R^3$ is 2-methyl-1-propenyl or isobutyl; A is oxygen or $NR^8$, wherein $R^8$ is hydrogen or an optionally substituted lower alkyl or aryl group; and $R^4$ is hydrogen, an optionally substituted hydrocarbon group or an optionally substituted acyl group; or a physiologically acceptable salt thereof, with a highly watersoluble cyclodextrin derivative, which comprises mixing the fumagillol derivative or physiologically acceptable salt thereof with the highly water-soluble cyclodextrin derivative in an aqueous solution, the concentration of the highly water-soluble cyclodextrin derivative being at about 100 mg/ml or more;

2. The method according to above paragraph 1, wherein $R^1$ and $R^2$ are combined to represent a chemical bond;

3. The method according to above paragraph 1, wherein $R^3$ is 2-methyl-1-propenyl;

4. The method according to above paragraph 1, wherein A is oxygen;

5. The method according to above paragraph 1, wherein $R^4$ is a substituted carbamoyl group;

6. The method according to above paragraph 1, wherein the fumagillol derivative is 6-O-(N-chloroacetylcarbamoyl)fumagillol;

7. The method according to above paragraph 1, wherein the fumagillol derivative is 6-O-(N-methylcarbamoyl)fumagillol;

8. The method according to above paragraph 1, wherein the highly water-soluble cyclodextrin derivative is a compound of the formula;

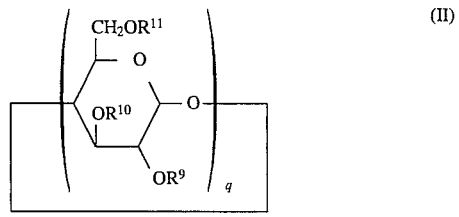

wherein q represents an integer of 6 to 12; $R^9$, $R^{10}$ and $R^{11}$ in respective repetition units are the same or different and are independently a dihydroxyalkyl group or a sugar residue;

9. The method according to above paragraph 8, wherein at least one of $R^9$, $R^{10}$ and $R^{11}$ is a sugar residue;

10. The method according to above paragraph 9, wherein the sugar residue is a member selected from the group consisting of glucosyl, maltosyl, maltotriosyl and dimaltosyl;

11. The method according to above paragraph 1, wherein the highly water-soluble cyclodextrin derivative is glucosyl-β-cyclodextrin;

12. The method according to above paragraph 1, wherein the highly water-soluble cyclodextrin derivative is maltosyl-β-cyclodextrin;

13. The method according to above paragraph 1, wherein the mole ratio between the highly water-soluble cyclodextrin derivative to the fumagillol derivative is in the range of about 1.5 to 3:1;

14. A complex of a fumagillol derivative of the formula:

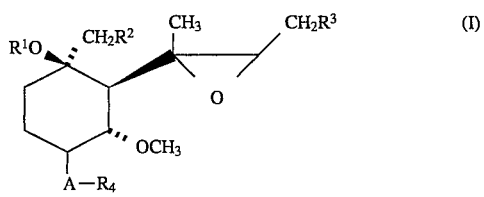

wherein $R^1$ is hydrogen; $R^2$ is halogen, $N(O)mR^5R^6$, $N+R^5R^6R^7.X—$ or $S(O)nR^5$, wherein $R^5$, $R^6$ and $R^7$ are independently an optionally substituted hydrocarbon group or an optionally substituted heterocyclic group; $X—$ is a counter anion; m is 0 or 1; n is an integer of 0 to 2; and $R^5$ and $R^6$ together with the adjacent nitrogen or sulfur atom may form an optionally substituted nitrogen- or sulfur-containing heterocyclic group which may form a condensed ring; or $R^1$ and $R^2$ are combined to represent a chemical bond; $R^3$ is 2-methyl-1-propenyl or isobutyl; A is oxygen or $NR^8$, wherein $R^8$ is hydrogen or an optionally substituted lower alkyl or aryl group; and $R^4$ is hydrogen, an optionally substituted hydrocarbon group or an optionally substituted acyl group; or physiologically acceptable salt thereof, with a highly water-soluble cyclodextrin derivative, which is produced by mixing the fumagillol derivative or a physiologically acceptable salt thereof with the highly water-soluble cyclodextrin derivative in an aqueous solution, the concentration of the highly water-soluble cyclodextrin derivative being at about 100 mg/ml or more;

15. The complex according to above paragraph 14, wherein $R^1$ and $R^2$ are combined to represent a chemical bond;

16. The complex according to above paragraph 14, wherein $R^3$ is 2-methyl- 1-propenyl group;

17. The complex according to above paragraph 14, wherein A is oxygen;

18. The complex according to above paragraph 14, wherein $R^4$ is a substituted carbamoyl group;

19. The complex according to above paragraph 14, wherein the fumagillol derivative is 6-O-(N-chloroacetylcarbamoyl)fumagillol;

20. The complex according to above paragraph 14, wherein the fumagillol derivative is 6-O-(N-methylcarbamoyl)fumagillol;

21. The complex according to above paragraph 14, wherein the highly water-soluble cyclodextrin derivative is a compound of the formula:

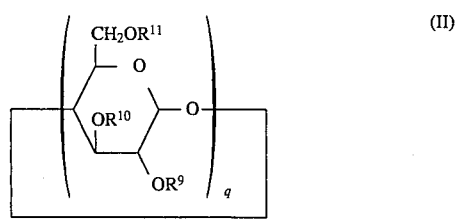

wherein q represents an integer of 6 to 12; $R^9$, $R^{10}$ and $R^{11}$ in respective repetition units are the same or different and are independently a dihydroxyalkyl group or a sugar residue;

22. The complex according to above paragraph 21, wherein at least one of $R^9$, $R^{10}$ and $R^{11}$ is a sugar residue;

23. The complex according to above paragraph 21, wherein the sugar residue is a member selected from the group consisting of glucosyl, maltosyl, maltotriosyl and dimaltosyl;

24. The complex according to above paragraph 14, wherein the highly water-soluble cyclodextrin derivative is glucosyl-β-cyclodextrin;

25. The complex according to above paragraph 14, wherein the highly water-soluble cyclodextrin derivative is maltosyl-β-cyclodextrin; and 26. The complex according to above paragraph 14, wherein the mole ratio between the highly water-soluble cyclodextrin to the fumagillol derivative is about 1.5 to 3:1.

DETAILED DESCRIPTION OF THE INVENTION

In the formula (I):

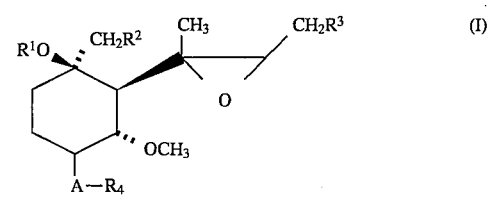

$R^2$ in the above formula (I) represents a halogen such as fluorine, chlorine, bromine or iodine. When $R^1$ and $R^2$ are combined to represent a chemical bond, they form an epoxy ring.

The hydrocarbon group represented by $R^5$, $R^6$ or $R^7$, which may have one or more substituents, is exemplified by straight or branched alkyl groups having 1 to 6 carbon atoms (e.g., methyl, ethyl, propyl, isopropyl, butyl, isobutyl, sec-butyl, pentyl, isopentyl, hexyl), alkenyl groups having 2 to 6 carbon atoms (e.g., vinyl, allyl, 2-butenyl, methylallyl, 3-butenyl, 2-pentenyl, 4-pentenyl, 5-hexenyl), alkynyl groups having 2 to 6 carbon atoms (e.g., ethynyl, propargyl, 2-butyn-1-yl, 3-butyn-2-yl, 1-pentyn-3-yl, 3-pentyn-1-yl, 4-pentyn-2-yl, 3-hexyn-1-yl), cycloalkyl groups having 3 to 6 carbon atoms (e.g., cyclopropyl, cyclobutyl, cyclopentyl, cyclohexyl), cycloalkenyl groups having 3 to 6 carbon atoms (e.g., cyclobutenyl, cyclopentenyl, cyclohexenyl, cyclohexadienyl), aralkyl groups having 7 to 13 carbon atoms(e.g., benzyl, 1-phenetyl, 2-phenetyl), and aryl groups having 6 to 10 carbon atoms (e.g., phenyl, naphthyl).

The heterocyclic group represented by $R^5$, $R^6$ or $R^7$, which may have one or more substituents, is exemplified by 5- or 6-membered heterocyclic groups having 1 to 4 hetero atoms (e.g., atoms of nitrogen, oxygen and sulfur) (e.g., 2-furyl, 2-thienyl, 4-thiazolyl, 4-imidazolyl, 4-pyridyl, 1,3,4-thiadiazol-2-yl, 1 -methyl-5-tetrazolyl). Further, the heterocyclic group may condense with a 5- or 6-membered ring (e.g., benzene, pyridine, cyclohexane) to form a condensed bicyclic group (e.g., 8-quinolyl, 8-purinyl).

Nitrogen-containing heterocyclic rings which may be formed by $R^5$ and $R^6$ together with the adjacent nitrogen atom include 4- to 7-membered nitrogen-containing heterocyclic rings (e.g., pyrrolidin-1-yl, piperazino, morpholino, 4-methylpiperazin-1-yl).

Sulfur-containing heterocyclic rings which may be formed by $R^5$ and $R^6$ together with the adjacent sulfur atom include 4- to 7-membered sulfur-containing heterocyclic rings (e.g., tetrahydrothiophen-1-yl, 1,4-thioxan-1-yl).

The nitrogen-containing or sulfur-containing heterocyclic ring which may be formed by $R^5$ and $R^6$ together with the adjacent nitrogen atom or sulfur atom may condense with a 5- or 6-membered ring (e.g., benzene, pyridine, pyrazine, pyridazine, cyclohexane) to form a condensed dicyclic group (e.g., isoindolyn-2-yl, 2-isoquinolyl, 1,3-dihydrobenzo[c]thiophen-2-yl, 2,3-dihydrobenzo[b]thiophen-1-yl, 3,4-dihydro-1H-2-benzopyran-2-yl, 3,4-dihydro-2H-1-benzopyran-1-yl, 1,2,4,5-tetrahydro-3-benzothiepin-3-yl, 1,3-dihydrothieno [3,4-c]pyridin-2-yl, 5,7-dihydrothieno [3,4-b]pyrazin-6-yl, 5,7-dihydrothieno [3,4-d]pyridazin-6-yl).

Lower alkyl groups represented by $R^8$, which may have one or more substituents, include alkyl groups having 1 to 6 carbon atoms (e.g., methyl, ethyl, propyl, isopropyl, butyl, isobutyl, sec-butyl, pentyl, isopentyl, hexyl).

Aryl groups represented by $R^8$, which may have one or more substituents, include aryl groups having 6 to 10 carbon atoms (e.g., phenyl, naphthyl).

Hydrocarbon groups represented by $R^4$, which may have one or more substituents, include the above-mentioned hydrocarbon groups represented by $R^5$, $R^6$, and $R^7$, each of which may have a substituent.

When the hydrocarbon group represented by $R^4$ is an alkenyl group, it preferably has no substituent.

Acyl groups represented by $R^4$, which may have one or more substituents, include acid residues (acyl groups derived from corresponding acids) such as acyl carboxylate, acyl sulfonate, carbamoyl, thiocarbamoyl and sulfamoyl, which may have a substituent, specifically alkanoyl, aroyl, heterocyclic carbonyl, carbamoyl, thiocarbamoyl, arylsulfonyl, alkylsulfonyl, sulfamoyl, alkoxyeabonyl and aryloxycarbonyl, each of which may have one or more substituents.

Alkanoyl groups as described above, which may have one or more substituents, include alkanoyl groups having 1 to 6 carbon atoms (e.g., formyl, acetyl, propionyl, isopropionyl, butyryl, pentanoyl, hexanoyl).

Aroyl groups which may have one or more substituents, include aroyl groups having 7 to 11 carbon atoms (e.g., benzoyl, 1-naphthoyl, 2-naphthoyl).

Heterocyclic carbonyl groups, which may have one or more substituents, include 5- or 6-membered heterocyclic carbonyl groups having 1 to 4 hetero atoms (e.g., atoms of nitrogen, oxygen and sulfur) (e.g., 2-furoyl, 2-thenoyl, nicotinyl, isonicotinyl).

Arylsulfonyl groups, which may have one or more substituents, include arylsulfonyl groups having 6 to 10 carbon atoms (e.g., benzenesulfonyl, 1-naphthylsulfonyl, 2-naphthylsulfonyl).

Alkylsulfonyl groups, which may have one or more substituents, include alkylsulfonyl groups having 1 to 6 carbon atoms (e.g., methylsulfonyl, ethylsulfonyl).

Alkoxycarbonyl groups, which may have one or more substituents, include alkoxycarbonyl groups having 2 to 7 carbon atoms (e.g., methoxycarbonyl, ethoxycarbonyl, isobutoxycarbonyl).

Aryloxycarbonyl groups, which may have one or more substituents, include aryloxycarbonyl groups having 7 to 11 carbon atoms (e.g., phenoxycarbonyl, 1-naphthyloxycarbonyl, 2-naphthyloxycarbonyl).

The hydrocarbon group or heterocyclic group represented by $R^5$, $R^6$ or $R^7$, each of which may have one or more substituents, the nitrogen-containing or sulfur-containing heterocyclic group which may be formed by $R^5$ and $R^6$ together with the adjacent nitrogen atom or sulfur atom and may be condensed, the lower alkyl group or aryl group represented by $R^8$, each of which may have one or more substituents, and the hydrocarbon group or acyl group represented by $R^4$, each of which may have one or more substituents (e.g., alkanoyl group, aroyl group, heterocyclic carbonyl group, carbamoyl group, thiocarbamoyl, arylsulfonyl group, alkylsulfonyl group, sulfamoyl group, alkoxycarbonyl group, aryloxycarbonyl group), may have 1 to 3 substituents at any of the possible positions.

Such substituents include $C_{1-6}$ alkyl groups (e.g., methyl, ethyl, propyl, isopropyl, butyl, isobutyl, sec-butyl, pentyl, isopentyl, hexyl), $C_{2-6}$ alkenyl groups (e.g., vinyl, allyl, 2-butenyl, methylallyl, 3-butenyl, 2-pentenyl, 4-pentenyl, 5-hexenyl), $C_{2-6}$ alkynyl groups (e.g., ethynyl, propargyl, 2-butyn-1-yl, 3-butyn-2-yl, 1-pentyl-3-yl, 3-pentyl-1-yl, 4-pentyl-2-yl, 3-hexyn-1-yl), $C_{3-6}$ cycloalkyl groups (e.g., cyclopropyl, cyclobutyl, cyclopentyl, cyclohexyl), $C_{3-6}$ cycloalkenyl groups (e.g., cyclobutenyl, cyclopentenyl, cyclohexenyl, cyclohexadienyl), $C_{6-10}$ aryl groups (e.g., phenyl, naphthyl), amino, $C_{1-6}$ alkylamino groups (e.g., methylamino, ethylamino, isopropylamino), di-$C_{1-6}$ alkylamino groups (e.g., dimethylamino, diethylamino), azide, nitro, halogens (e.g., fluorine, chlorine, bromine, iodine), hydroxyl, $C_{1-4}$ alkoxy groups (e.g., methoxy, ethoxy), $C_{6-10}$ aryloxy groups (e.g., phenyloxy, naphthyloxy), $C_{1-6}$ alkylthio groups (e.g., methylthio, ethylthio, propylthio), $C_{6-10}$ arylthio groups (e.g., phenylthio, naphthylthio), cyano, carbamoyl group, carboxyl group, $C_{1-4}$ alkoxycarbonyl groups (e.g., methoxycarbonyl, ethoxycarbonyl), $C_{7-11}$ aryloxycarbonyl groups (e.g., phenoxycarbonyl, 1-naphthyloxycarbonyl, 2-naphthyloxycarbonyl), carboxyl-$C_{1-4}$ alkoxy groups (e.g., carboxymethoxy, 2-carboxyethoxy), $C_{1-6}$ alkanoyl groups (e.g., formyl, acetyl, propionyl, isopropionyl, butyryl, pentanoyl, hexanoyl), $C_{7-11}$ aroyl groups (e.g., benzoyl, 1-naphthoyl, 2-naphthoyl), $C_{6-10}$ arylsulfonyl groups (e.g., benzenesulfonyl, 1-naphthylsulfonyl, 2-naphthylsulfonyl), $C_{1-6}$ alkylsulfinyl groups (e.g., methylsulfinyl, ethylsulfinyl), $C_{6-10}$ arylsulfinyl groups (e.g., benzenesulfinyl, 1-naphthylsulfinyl, 2-naphthylsulfinyl), $C_{1-6}$ alkylsulfonyl groups (e.g., methylsulfonyl, ethylsulfonyl), 5- or 6-membered heterocyclic groups having 1 to 4 hetero atoms (e.g., atoms of nitrogen, oxygen and sulfur) (e.g., 2-furyl, 2-thienyl, 4-thiazolyl, 4-imidazolyl, 4-pyridyl, 1,3,4-thiadiazol-2-yl, 1-methyl-5-tetrazolyl), 5- or 6-membered heterocyclic carbonyl groups having 1 to 4 hetero atoms (e.g., atoms of nitrogen, oxygen and sulfur) (e.g., 2-furoyl, 2-thenoyl, nicotinyl, isonicotinyl), and 5- or 6-membered heterocyclic thio groups having 1 to 4 hetero atoms (e.g., atoms of nitrogen, oxygen and sulfur) (e.g., 4-pyridylthio, 2-pyrimidylthio, 1,3,4-thiadiazol-2-ylthio, 1-methyl-5-tetrazolylthio), which heterocyclic thio groups may condense with a benzene ring to form a condensed bicyclic thio group (e.g., 2-benzothiazolylthio, 8-quinolylthio). Also, provided that $R^4$ represents a di-substituted carbamoyl group, thiocarbamoyl group or sulfamoyl group, it may form a nitrogen-containing heterocyclic ring (e.g., pyrrolidin-1-yl, piperidino, morpholino, piperazin-1-yl, 4-methylpiperazin-1-yl, 4-phenylpiperazin-1-yl) together with the nitrogen atom of the carbamoyl group, thiocarbamoyl group or sulfamoyl group.

The respective substituents of the following groups may in turn have 1 to 3 substituents at any of the possible positions: 1) the substituent in the hydrocarbon group or heterocyclic group represented by $R^5$, $R^6$ or $R^7$, each of which may have one or more substituents; 2) the substituent in the nitrogen-containing or sulfur-containing heterocyclic group which may be formed by $R^5$ and $R^6$ together with the adjacent nitrogen atom or sulfur atom and may be condense; 3) the substituent in the lower alkyl group or aryl group represented by $R^8$, each of which may have one or more substituents; and 4) the substituent in the hydrocarbon group, alkanoyl group, aroyl group, heterocyclic carbonyl group, carbamoyl group, thiocarbamoyl, arylsulfonyl group, alkylsulfonyl group, sulfamoyl group, alkoxycarbonyl group or aryloxycarbonyl group represented by $R^4$, each of which may have one or more substituents.

Such substituents include the above-mentioned $C_{1-6}$ alkyl groups, $C_{2-6}$ alkenyl groups, $C_{2-6}$ alkynyl groups, $C_{3-6}$ cycloalkyl groups, $C_{3-6}$ cycloalkenyl groups, $C_{6-10}$ aryl groups, amino group, $C_{1-6}$ alkylamino groups, di-$C_{1-6}$ alkylamino groups, azide group, nitro group, halogens, hydroxyl group, $C_{1-4}$ alkoxy groups, $C_{6-10}$ aryloxy groups, $C_{1-6}$ alkylthio groups, $C_{6-10}$ arylthio groups, cyano group, carbamoyl group, carboxyl group, $C_{1-4}$ alkoxycarbonyl groups, $C_{7-11}$ aryloxycarbonyl groups, carboxyl-$C_{1-4}$ alkoxy groups, $C_{1-6}$ alkanoyl groups, $C_{7-11}$ aroyl groups, $C_{6-10}$ arylsulfonyl groups, $C_{1-6}$ alkylsulfinyl groups, $C_{6-10}$ arylsulfinyl groups, $C_{1-6}$ alkylsulfonyl groups, 5- or 6-membered heterocyclic groups, 5- or 6-membered heterocyclic carbonyl groups and 5- or 6-membered heterocyclic thio groups.

Example counter anions represented by $X^-$ include halogen ions (e.g., iodine ion, bromine ion, chlorine ion), sulfur ion, phosphate ion, nitrate ion, perchlorate ion, tetrafluoroborate ion, methanesulfate ion, p-tolylsulfate ion, benezenesulfate ion, hydroxyl ion, organic acid carboxylate ion (e.g., oxalate ion, maleate ion, fumarate ion, succinate ion, citrate ion, lactate ion, trifluoroacetate ion, lactobionate ion, acetate ion, propionate ion, tartrate ion, ethylsuccinate ion).

In the fumagillol derivative (I), $R^1$ and $R^2$ are preferably combined to represent a chemical bond or $R^1$ is hydrogen and $R^2$ is $N(O)mR^5R^6$, $N+R^5R^6R^7.X-$ or $S(O)nR^5$ (wherein $R^5$, $R^{6,}$ $R^{7,}$ m, n and X— are the same meaning as defined above). Most preferably, $R^1$ and $R^2$ are combined to represent a chemical bond. A is preferably oxygen or NH. Most preferably, A is oxygen. $R^3$ is preferably 2-methyl-1-propenyl. $R^4$ is preferably substituted carbamoyl group. The substituent on the carbamoyl group is preferably a optionally halogenated an alkanoyl group having 1 to 6 carbon atoms or an alkyl group having 1 to 6 carbon atoms.

Examples of preferred fumagillol derivative (I) include 6-O-(N-chloroacetylcarbamoyl) fumagillol, 6-O-(N-methylcarbamoyl)fumagillol, 6α-(N'-chloroacetylureido)-6-deoxyfumagillol-4-(N-chloroacetylcarbamoyloxy)- 2-(1,2-epoxy-1,5-methyl-4-hexenyl)-1-(1,3-dihydrobenzo[C]thiophen-2-ylio)- 3-methoxycyclohexanol chloride. Among these, 6-O-(N-chloroacetylcarbamoyl) fumagillol and 6-O-(N-methylcarbamoyl)fumagillol are most preferable.

Having an asymmetric center in the molecule thereof, fumagillol derivative (I) exhibits optical activity. Its absolute configuration is based on the starting material fumagillol and is identical with the absolute configuration of fumagillol unless otherwise stated. The mode of bonding of the substituent on the cyclohexane ring is as follows:
wherein ... represents an α-bond, ▬ represents a β-bond, and —may be an α-bond or a β-bond.

When that fumagillol derivative (I) has an acidic substituent (e.g., carboxyl) or a basic substituent (e.g., amino, lower alkylamino, di- lower alkylamino, nitrogen-containing heterocyclic group) in the molecule thereof, it may be used as a physiologically acceptable salt: Such physiologically acceptable salts include salts with an inorganic base, salts with an organic base, salts with an inorganic acid, salts with an organic acid and salts with basic or acidic amino acids. Inorganic bases capable of forming such salts include alkali metals (e.g., sodium, potassium) and alkaline earth metals (e.g., calcium, magnesium). Organic bases capable of forming such salts include trimethylamine, triethylamine, pyridine, picoline, N,N-dibenzylethylenediamine, ethanolamine, diethanolamine, trishydroxymethylaminomethane and dicyclohexylamine. Inorganic acids capable of forming such salts include hydrochloric acid, hydrobromic acid, sulfuric acid, nitric acid and phosphoric acid. Organic acids capable of forming such salts include formic acid, acetic acid, trifluoroacetic acid, oxalic acid, tartaric acid, fumaric acid, maleic acid, methanesulfonic acid, benzenesulfonic acid and p-toluenesulfonic acid. Basic or acidic amino acids capable of forming such salts include arginine, lysine, ornithine, aspartic acid and glutamic acid. Of these salts, those with a base (i.e., salts with an inorganic base, salts with an organic base, salts with a basic amino acid) are salts which can be formed with the carboxyl group among the substituents for fumagillol derivative (I), and those with an acid (i.e., salts with an inorganic acid, salts with an organic acid, salts with an acidic amino acid) are salts which can be formed with, for example, the amino group, lower alkylamino group, di-lower alkylamino group or nitrogen-containing heterocyclic group among the substituents for the fumagillol derivative (I).

Also, when the fumagillol derivative (I) has a di- lower alkylamino group, nitrogen-containing heterocyclic group or nitrogen-containing aromatic heterocyclic group in the molecule thereof, the nitrogen atom in these substituents may be further alkylated to form a quaternary ammonio group (e.g., trimethylammonio, N-methylpyridinio, N-methylpyrrolidin-1-ylio), with counter artions including the same counter anions as specified for $X^-$ above.

The fumagillol derivative (I) or a salt thereof can be produced by using fumagillol, the hydrolyzate of microbially produced fumagillin [Tarbell, D. S. et al., Journal of American Chemical Society, 83, 3096 (1961)] as the starting material. Methods of its production and its physical, chemical and biological properties are described in detail in EP-A-359,036, EP-A-357,061, EP-A- 354,787, EP-A-386, 667, EP-A-415,294 and other publications.

The highly water-soluble cyclodextrin derivative for the present invention is preferably a compound resulting from the replacement of the hydrogen atoms of some or all of the hydroxyl groups at the 2-, 3- and 6-positions of the glucose of a cyclic oligosaccharide comprising 6 to 12 glucose units with another functional group (e.g., dihydroxyalkyl group, sugar residue, hydroxyalkyl group).

Said highly water-soluble cyclodextrin derivative (hereinafter also referred to as CyD) is about 100 mg/ml or more, preferably about 130 mg/ml or more in water solubility.

Examples of desirable highly water-soluble cyclodextrin derivatives include the compounds represented by the formula:

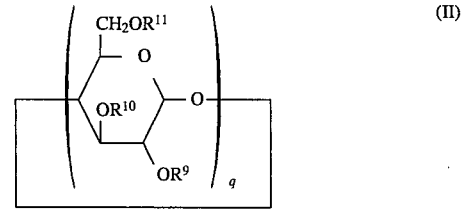

(II)

wherein q represents an integer of 6 to 12; $R^9$, $R^{10}$ and $R^{11}$ independently represent a dihydroxyalkyl group or a sugar residue, whether identical or not in each repeat unit. Preferably, ether derivatives of hydroxyl group of α-CyD (q=6), β-CyD (q=7), γ-CyD (q=8), δ-CyD (q=9) are included. Among these, the ether derivative of hydroxyl group of β-CyD is most preferable.

Dihydroxyalkyl groups represented by $R^9$ through $R^{11}$ include dihydroxy-$C_{1-6}$ alkyl groups (e.g., dihydroxymethyl, 2,2-dihydroxyethyl, 2,2-dihydroxypropyl, 2,2-dihydroxypentyl, 2,2-dihydroxyhexyl). Among these, dihydroxy-$C_{1-4}$ alkyl groups (e.g., dihydroxymethyl, 2,2-dihydroxyethyl, 2,2-dihydroxypropyl) are most preferable.

Sugar residues represented by $R^9$ through $R^{11}$ include $C_{3-24}$ sugar residues (e.g., erythrosyl, treosyl, arabinosyl, ribosyl, glucosyl, galactosyl, glycero-gluco-heptosyl, maltosyl, lactosyl, real totriosyl, dimal tosyl ), with preference given to $C_{6-24}$ sugar residues (e.g., glucosyl, galactosyl, glycero-gluco-heptosyl, maltosyl, lactosyl, maltotriosyl, dimaltosyl). Among these, $C_{6-12}$ sugar residues (e.g., glucosyl, galactosyl, glycero-gluco-heptosyl, maltosyl, lactosyl) are most preferable.

More desirable highly water-soluble cyclodextrin derivatives include the compounds represented by formula (II) wherein at least one of $R^9$ through $R^{11}$ is a sugar residue. Examples of such compounds include glucosyl-α—, —β—, —γ— and —δ-CyD, maltosyl-α—, —β—, —γ— and —δ-CyD, maltotriosyl-α—, —β—, —γ- and —δ-CyD and dimaltosyl-α—, —β—, —γ— and —δ-CyD. Among these, glucosyl-α—, —β—, —γ— and —δ-CyD and maltosyl-α—, —β—, —γ— and —δ-CyD are more preferable. Glucosyl-β-CyD and maltosyl-β-CyD are most preferable.

These highly water-soluble cyclodextrin derivatives may be used singly or in combination of two or more kinds.

The amount of highly water-soluble cyclodextrin derivative to be used is preferably about 1 to 5 mols, more preferably about 1.5 to 3 mols per mol of the fumagillol derivative (I) or salt thereof.

Concerning the form of the complex of the present invention, the fumagillol derivative (I) or salt thereof is more stable in a solid state, and it is preferable to prepare the complex as a powder by distilling off the water which is present by itself. Methods of distillation include lyophilization and drying under reduced pressure and, as the case may be, evaporation under normal pressure. For stabilization of the fumagillol derivative (I) or salt thereof, lyophilization or freezing followed by drying under reduced pressure is appropriate.

For producing the complex of the present invention, a fumagillol derivative (I) (or a salt thereof) and a highly water-soluble cyclodextrin derivative are made into the state of solution in water or buffer normally at room temperature (−5° to 35° C.). Said solution can be obtained by: for example, a) mixing a water or buffer solution of a highly water-soluble cyclodextrin derivative with a fumagillol derivative (I) (or a salt thereof); b) mixing a water or buffer solution of a highly water-soluble cyclodextrin derivative with a water or buffer suspension of a fumagillol derivative (I) (or a salt thereof); c) mixing a highly water-soluble cyclodextrin derivative and a fumagillol derivative (I) (or a salt thereof) with water or buffer; d) mixing a highly water-soluble cyclodextrin derivative with a water and buffer suspension of a fumagillol derivative (I) (or a salt thereof). The solutions or suspensions may be cooled or warmed if necessary. The concentration of highly water-soluble cyclodextrin derivative is preferably about 100 mg/ml or more, more preferably about 130 mg/ml or more. It is preferable to add the fumagillol derivative (I) or salt thereof to the aqueous solution of the highly water-soluble cyclodextrin derivative so that the amount of the highly water-soluble cyclodextrin derivative in the aqueous solution will be about 1 to 5 mols, preferably about 1.5 to 3 mols per mol of the fumagillol derivative (I) or salt thereof, as stated above.

When the suspension of the fumagillol derivative (I) or salt thereof is stirred, the fumagillol derivative (I) or salt thereof dissolves gradually. It is preferable to continue stirring for over 1 minute and stop stirring upon completion of the progress of dissolution. If any portion remains undissolved, the solution is filtered to yield a complex containing the fumagillol derivative (I) with improved solubility. For powdering said complex, the solution obtained is lyophilized or dried under reduced pressure or normal pressure.

After the fumagillol derivative (I) or salt thereof is added, if necessary, an alkaline substance can be added to the resulting suspension or solution so as to stabilize the fumagillol derivative or salt thereof.

Examples of the alkaline substance include inorganic salts such as alkali metal hydroxides (e.g., sodium hydroxide, potassium hydroxide, etc.), alkali metal hydrogen carbonates (e.g., sodium hydrogen carbonate, potassium hydrogen carbonate, etc.), alkali metal carbonates (e.g., sodium carbonate, potassium carbonate, etc.), alkali metal phosphate derivatives (e.g., sodium phosphate, tribasic; sodium phosphate, dibasic; potassium phosphate, tribasic; potassium phosphate, dibasic; etc.); organic basic substances such as alkali metal salts of organic mono carboxylic acids (e.g., sodium acetate, potassium acetate, etc.).

The mount of the alkaline substance to be used is preferably about 0.0002 to 0.2 mols per mol of the fumagillol derivative (I) or salt thereof. Most preferably, the mount of the alkaline substance to be used is about 0.001 to 0.035 mols per mol of the fumagillol derivative (I) or salt thereof.

The alkaline substance can be used as it is, or alternatively, used as an aqueous solution thereof at appropriate concentration.

The powder obtained through the above procedure is an inclusion compound or a complex based on static, hydrophobic interaction or hydrogen bond. Also, the powder may contain the fumagillol derivative (I) or salt thereof and/or the highly water-soluble cyclodextrin derivative in addition to the inclusion compound or complex. Such powder is also included in the scope of the complex of the present invention.

The complex of the present invention can be used as a parenteral preparation. The parenteral preparation can be produced as follows.

To improve various properties (e.g., vial packing quality, specific volume, antistatic property) of the powder obtained, sugars (e.g., glucose, mannitol, inositol, etc.), preservatives (e.g., methyl-paraben, propyl-paraben, benzyl alcohol, chlorobutanol, etc.), isotonizing agent (e.g., sodium chloride, glycerin, sorbitol, glucose, etc.), antistatic agents (e.g., magnesium stealate, etc.) for use in injection may be added. The powder thus obtained is easily soluble in distilled water for injection and in aqueous solutions prepared with sodium chloride and, sugars (e.g., glucose, mannitol, inositol) or a dispersing agent (e.g., Tween 80 (Atlas Powder, U.S.A.), HCO-60 (Nikko Chemicals), carboxymethyl cellulose, sodium alginate, etc.). After dissolution, a fumagillol derivative (I) or a salt thereof at a concentration effective against the target disease, in the form of a preparation for injection, can be administered intravenously, intramuscularly, subcutaneously, intraviscerally (e.g., hepatic artery) or into tumors and other lesions.

Also, the powder obtained according to the present invention can be prepared in non-injection dose forms such as topical preparations (e.g., nasal preparation, dermatological preparation) and suppositories (e.g., rectal, vaginal) for use in the field of pharmaceutics.

A topical preparation from the powder obtained according to this invention may be provided in a solid, semi-solid or liquid state in the conventional manner. To manufacture the solid topical preparation for instance, the powder itself or together with an excipient (e.g., glucose, mannitol, starch, microcrystalline cellulose, etc.) and/or thickener (e.g., natural mucilages, cellulose derivatives, polyacrylates, etc.) are processed into a powdery composition. To make a liquid composition, the powders obtained according to the present invention are processed into an oily or aqueous solution in substantially the same manner as in the case of injections. The semi-solid preparation may be an aqueous or oily gel or ointment. In any case, there may be added a pH adjusting agent (e.g., carbonic acid, phosphoric acid, citric acid, hydrochloric acid, sodium hydroxide, etc.), a preservative (e.g., p-hydroxybenzoic acid esters, chlorobutanol, benzalkonium chloride, etc.), etc.

A suppository of the powder obtained according to this invention, whether in oily or aqueous solid or semi-solid state or in liquid state, may be produced in the per se conventional manner. As examples of the kind of oleagenous base for such a composition, higher fatty acid glycerides [e.g., cacao butter, Witepsol (Dynamit-Novel, Germany), etc.], intermediate fatty acids [e.g., Miglyol (Dynamit-Novel), etc.] and vegetable oils (e.g., sesame oil, soybean oil, cottonseed oil, etc.) may be mentioned. The aqueous base is exemplified by polyethylene glycol and propylene glycol, while the aqueous gel base may be selected from among natural mucilages, cellulose derivatives, vinyl polymers, polyacrylates, etc.

The complex of the present invention inhibits anglogenesis, and exhibits potent pharmacological action such as therapeutic and prophylactic effects on various inflammatory diseases (e.g., arthrorheumatis), diabetic retinopathy and tumors (e.g. cancer such as mastocarcinoma, hepatoma, large intestinal cancer and Kaposi's sarcoma), with low toxicity. It is useful as a drug for mammals (e.g., monkeys, bovines, dogs, humans) to prevent or treat diseases such as various inflammatory diseases (e.g., arthrorheumatis), diabetic retinopathy and tumors (e.g., cancer such as mastocarcinoma, hepatoma, large intestinal cancer and Kaposi's sarcoma).

When administering the complex of the present invention by injection for the purpose of treating an adult patient having a tumor (body weight of 50 kg), for instance, the amount per dose, which varies depending on the type, activity and other factors of the fumagillol derivative (I) or salt thereof, can be selected from the range of about 1.0 mg to 5.0 g, preferably about 25 mg to 2.0 g, more preferably about 50 mg to 1.0 g daily.

EXAMPLES

The present invention is hereinafter described in more detail by means of the following comparative examples and working examples, which are not to be construed as limitative of the invention.

Comparative Example 1

To a 5 ml aqueous solution containing 1000 mg of maltosyl-β-cyclodextrin (hereinafter abbreviated G2βCyD) was added 250 mg of 6-O-(N-chloroacetylcarbamoyl) fumagillol (hereinafter abbreviated TNP-470), followed by stirring at 25° C. for 8 hours to obtain a solution. The undissolved portion of TNP-470 was filtered out, and the filtrate was placed in a vial and lyophilized in accordance with a conventional method to yield a powder. To the entire amount of the powder thus obtained, 5 ml of water was added to yield a uniform aqueous solution. Separately, in accordance with the conventional method, 110 mg of G2βCyD was dissolved in 5 ml of water; 250 mg of TNP-470 was added to this solution, followed by stirring at 25° C. for 8 hours. Then, the solution was filtered. The above uniform solution and the filtered solution were assayed for TNP-470 by high performance liquid chromatography (HPLC). Also, the saturation solubility of TNP-470 alone was determined by HPLC. The results shown in Table 1 were obtained. The solubility showed almost no improvement in the conventional method, while a marked improvement occurred in the method of the present invention.

Conditions for HPLC

Column: ODS, YMC-Pack A-312 (Yamamura Chemical Laboratories)

Mobil phase: water-acetonitrile (1:1 v/v)

Flow rate: 1.0 ml/min.

Detector: Ultra violet detector (wavelength: 210 nm)

TABLE 1

| Comparison of Solubility | |
|---|---|
| The present invention | 36.7 mg/ml |
| Conventional method | 6.7 |
| TNP-470 alone | 1.9 |

Comparative Example 2

To a 5 ml aqueous solution containing 500 mg of glucosyl-β-cyclodextrin (hereinafter abbreviated G1[CyD]) was added 250 mg of TNP- 470, followed by stirring at 25° C. for 8 hours to obtain a solution. The resulting aqueous solution was filtered and lyophilized in accordance with the standard method to yield a powder. To the entire amount of the powder thus obtained, 5 ml of water was added to yield a uniform aqueous solution. Separately, in accordance With the conventional method, 100 mg of G1βCyD was dissolved in 5 ml of water; 250 mg of TNP-470 was added to this solution, followed by stirring at 25° C. for 8 hours. Then, the solution was filtered. The above uniform solution and the filtered solution were assayed for TNP-470 by HPLC method as described in Comparative Example 1. Also, the saturation solubility of TNP-470 alone was determined by HPLC. The results shown in Table 2 were obtained. The solubility showed almost no improvement in the conventional method, while a marked improvement occurred in the method of the present invention.

TABLE 2

| Comparison of Solubility | |
|---|---|
| The present invention | 23.1 mg/ml |
| Conventional method | 6.5 |
| TNP-470 alone | 1.9 |

Example 1

To a 5 ml aqueous solution containing 1000 mg of maltosyl-β-cyclodextrin 1 was added 100 mg of TNP-470, followed by stirring at 25° C. for 30 minutes to yield a solution. This aqueous solution was filtered, and 5 ml of the filtrate was placed in a vial and lyophilized to yield a powder.

Example 2

To a 5 ml aqueous solution containing 750 mg of maltosyl-β-cyclodextrin was added 100 mg of TNP-470, followed by stirring at 25° C. for 30 minutes to yield a solution. This aqueous solution was filtered, and 5 ml of the filtrate was placed in a vial and lyophilized to yield a powder.

Example 3

To a 5 ml aqueous solution containing 500 mg of maltosyl-β-cyclodextrin was added 100 mg of TNP-470, followed by stirring at 25° C. for 30 minutes to yield a solution. This aqueous solution was filtered, and 5 ml of the filtrate was placed in a vial and lyophilized to yield a powder.

Example 4

To a 5 ml aqueous solution containing 750 mg of glucosyl-β-cyclodextrin was added 100 mg of TNP-470, followed by stirring at 25° C. for 30 minutes to yield a solution. This aqueous solution was filtered, and 5 ml of the filtrate was placed in a vial and lyophilized to yield a powder.

Example 5

To a 5 ml aqueous solution containing 500 mg of glucosyl-β-cyclodextrin was added 100 mg of TNP-470, followed by stirring at 25° C. for 30 minutes to yield a solution. This aqueous solution was filtered, and 5 ml of the filtrate was placed in a vial and lyophilized to yield a powder.

Example 6

To a 5 ml aqueous solution containing 726 mg of maltosyl-β-cyclodextrin was added 100 mg of TNP-470, followed by stirring at 25° C. for 180 minutes to yield a solution. This aqueous solution was filtered, and 5 ml of the filtrate was placed in a vial and lyophilized to yield a powder. The stability of this powder and that of TNP-470 alone were compared after storage at 40° C. for i month. TNP-470 was quantified by HPLC. The results are shown in Table 3. The powder according to the present invention was found to be very stable.

TABLE 3

| Stability | |
|---|---|
| | Percent residence |
| The present invention | 96% |
| TNP-470 alone | 68% |

Example 7

Maltosyl-β-cyclodextrin (719g) was dissolved in water (4950 ml) in a beaker (10 liters capacity). To this solution was added TNP-470 (99 g), followed by stirring at 25° C. for 3 hours. Upon completion of the progress of dissolution, the resulting solution was filtered through a filter having a pore size of 0.22 μm. The filtrate was filled in 5 ml portions into vials, followed by lyophilization to give a preparation for injection.

Example 8

Maltosyl-β-cyclodextrin (72.3 g) was dissolved in water (400 ml) in a beaker (10 liters capacity). To this solution was added TNP-470 (10 g), followed by stirring at 25° C. for 1.5 hours. To this was added 0.1N NaOH (0.9 ml), followed by stirring at 25° C. for 1.5 hours. Upon completion of the progress of dissolution, water was added to the resulting solution to make up a total of 500 ml, and the solution was then filtered through a filter having a pore size of 0.22 μm. The filtrate was subjected to lyophilization to give a preparation for infection. The stability of this preparation was studied after storage at 40° C. for 1 month. TNP-470 was quantified by the same HPLC method as described in Comparative Example 1. The percent residue of TNP- 470 was 97%. The preparation according to the present invention was found to be very stable.

Example 9

Except that 5.4ml of 0.1N NaOH was used instead of 0.9ml of 0.1N NaOH, the procedure of Example 8 was followed to give a preparation con raining TNP-470 (30 mg).

Example 10

Except that 0.6 ml of 0.1N KOH was used instead of 0.9 ml of 0.1N NaOH, the procedure of Example 8 was followed to give a preparation containing TNP-470 (30 mg).

The production method of the present invention is industrially feasible, and the complex obtained by the production method of the present invention is easily soluble in water, highly stable in storage and can be used as a preparation for injection.

What is claimed is:

1. A complex of (a) 6-O-(N-chloroacetylcarbamoyl)fumagillol or a physiologically acceptable salt thereof, (b) a water soluble cyclodextrin derivative, and (c) an alkaline substance;

the physiologically acceptable salt being selected from salts with an inorganic base, salts with an organic base, salts with an inorganic acid, salts with organic acid, and salts with basic and acidic amino acids;

the water soluble cyclodextrin derivative being selected from the group consisting of glucosyl-α-cyclodextrin, glucosyl-β-cyclodextrin, glucosyl-γ-cyclodextrin, glucosyl-δ-cyclodextrin, maltosyl-α-cyclodextrin, maltosyl-β-cyclodextrin, maltosyl-γ-cyclodextrin, maltosyl-δ-cyclodextrin, maltotriosyl-α-cyclodextrin, maltotriosyl-β-cyclodextrin, maltotriosyl-γ-cyclodextrin, maltotriosyl-δ-cyclodextrin, dimaltosyl-α-cyclodextrin, dimaltosyl-β-cyclodextrin, dimaltosyl-γ-cyclodextrin, dimaltosyl-δ-cyclodextrin; and the complex being produced by mixing (a), (b) and (c) in an aqueous solution, the concentration of (b) in the aqueous solution being about 100 mg/ml or more.

2. The complex according to claim 1, wherein the water soluble cyclodextrin derivative is glucosyl-β-cyclodextrin.

3. The complex according to claim 1, wherein the water-soluble cyclodextrin derivative is maltosyl-β-cyclodextrin.

4. The complex according to claim 1, wherein the water-soluble cyclodextrin derivative is used in an amount of about 1.5 to 3 moles per mole of the 6-O-(N-chloroacetylcarbamoyl) fumagillol or a physiologically acceptable salt thereof.

5. The complex according to claim 1, wherein the alkaline substance is used in an amount of about 0.0002 to 0.2 moles per mole of the 6-O-(N-chloroacetylcarbamoyl)fumagillol or a physiologically acceptable salt thereof.

* * * * *